United States Patent
Kaufmann et al.

(10) Patent No.: US 8,859,740 B2
(45) Date of Patent: Oct. 14, 2014

(54) ANTI-INFECTIVE BINDING PROTEINS THAT BIND AIP2

(71) Applicants: Gunnar F. Kaufmann, San Diego, CA (US); Heyue Zhou, San Diego, CA (US); Guodi Lu, San Diego, CA (US)

(72) Inventors: Gunnar F. Kaufmann, San Diego, CA (US); Heyue Zhou, San Diego, CA (US); Guodi Lu, San Diego, CA (US)

(73) Assignee: Sorrento Therapeutics Inc., San Diego, CA (US)

( * ) Notice: Subject to any disclaimer, the term of this patent is extended or adjusted under 35 U.S.C. 154(b) by 0 days.

(21) Appl. No.: 14/062,774

(22) Filed: Oct. 24, 2013

(65) Prior Publication Data

US 2014/0120093 A1    May 1, 2014

Related U.S. Application Data

(60) Provisional application No. 61/719,103, filed on Oct. 26, 2012.

(51) Int. Cl.
*C07K 16/12* (2006.01)
*A61K 39/40* (2006.01)

(52) U.S. Cl.
CPC ......... *C07K 16/1271* (2013.01); *C07K 2317/76* (2013.01); *C07K 2317/21* (2013.01)
USPC ................. 530/387.3; 424/133.1; 424/135.1; 424/165.1; 530/389.5

(58) Field of Classification Search
CPC combination set(s) only.
See application file for complete search history.

(56) References Cited

U.S. PATENT DOCUMENTS

| | | |
|---|---|---|
| 2010/0291093 A1 | 11/2010 | Janda et al. |
| 2012/0107327 A1 | 5/2012 | Anderson et al. |

FOREIGN PATENT DOCUMENTS

| | | |
|---|---|---|
| WO | 2011127032 | 10/2011 |

OTHER PUBLICATIONS

Lederman et al (Molecular Immunology 28:1171-1181, 1991).*
Li et al (Proc. Natl. Acad. Sci. USA 77:3211-3214, 1980).*
Rudikoff et al (Proc. Natl. Acad. Sci. USA, 79(6):1979-1983, Mar. 1982).*
Paul, Fundamental Immunology, 3rd edition, 1993, pp. 292-295.*
Colman P. M. (Research in Immunology, 145:33-36, 1994).*
MacCallum et al (J. Mol. Biol., 262,732-745, 1996).*
Casset et al (Biochemical and Biophysical Research Communications, 307:198-205, 2003).*
Bendig M. M. (Methods: A Companion to Methods in Enzymology, 1995; 8:83-93).*
Lyon et al., "Rational design of a global inhibitor of the virulence response in *Staphylococcus aureus*, based in part on localization of the site of inhibition to the receptor-histidine kinase, AgrC" PNAS 97:13330-13335, 2000.
Kaufmann et al. "Generation of Quorum Quenching Antibodies" Chap 22 Quorum Sensing: Methods and Protocols, Methods in Molecular Biology, vol. 692, DOI 10.1007/978-1-60761-971-0_22, © Springer Science+Business Media, LLC 2011.
Park et al. "Infection Control by Antibody Disruption of Bacterial Quorum Sensing Signaling" Chemistry and Biology 14:1119-1127, 2007.

* cited by examiner

*Primary Examiner* — Padma V Baskar
(74) *Attorney, Agent, or Firm* — Jeffrey B. Oster

(57) ABSTRACT

There is disclosed compositions and methods relating to or derived from anti-AIP2 antibodies. More specifically, there is disclosed fully human antibodies that bind AIP2, AIP2-binding fragments and derivatives of such antibodies, and AIP2-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having AIP2 related disorders or conditions. There is also disclosed a method to treat *S. aureus* infections by administering an anti-AIP2 antibody described herein.

5 Claims, 3 Drawing Sheets

ANTI-INFECTIVE BINDING PROTEINS THAT BIND AIP2

CROSS REFERENCE TO RELATED APPLICATION

This patent application claims priority from U.S. Provisional Patent application 61/719,103 filed 26 Oct. 2012.

The present invention was made with partial support of NIH grant 1R42AI098182. The Federal Government has certain rights in this invention.

TECHNICAL FIELD

The present disclosure provides compositions and methods relating to or derived from anti-auto-inducing peptide (AIP) 2 antibodies. More specifically, the present disclosure provides human antibodies that bind AIP2, AIP2-binding fragments and derivatives of such antibodies, and AIP2-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having AIP2 related bacterial infections, including infections caused by *Staphylococcus aureus* in general and particularly methicillin-resistant *Staphylococcus aureus* (MRSA).

BACKGROUND

Ever since it was first discovered by Sir Alexander Ogston in 1880, *Staphylococcus aureus* has been regarded as a serious threat to human health, capable of causing a multitude of infections. The rise of antibiotic-resistant strains in the 1960s and 1970s, particularly methicillin-resistant *S. aureus* (MRSA), has created additional therapeutic challenges. Currently, MRSA strains account for >50% of all *S. aureus* isolates causing clinical disease in the US. This is a much higher percentage compared to other countries, such as France at 14.5% and the Netherlands at 3.1%. In a review of 31 observational studies from Western Europe, the authors found that the percentage of MRSA among *S. aureus* clinical isolates ranged between 5% and 54%, but was limited by the different methodologies used in the studies.

Methicillin-resistant *Staphylococcus aureus* (MRSA) is a bacterium responsible for several difficult-to-treat infections in humans. It is also called multidrug-resistant *Staphylococcus aureus* and oxacillin-resistant *Staphylococcus aureus* (ORSA). MRSA is any strain of *Staphylococcus aureus* that has developed resistance to beta-lactam antibiotics, which include the penicillins (such as methicillin, dicloxam, nafcillin and oxacillin) and the cephalosporins. Strains unable to resist these antibiotics are classified as methicillin-sensitive *Staphylococcus aureus* (MSSA). The development of such resistance does not cause the organism to be more intrinsically virulent than strains of *Staphylococcus aureus* that have no antibiotic resistance, but resistance does make MRSA infection more difficult to treat with standard types of antibiotics and thus more dangerous.

MRSA is especially troublesome in hospitals, prisons, schools, and nursing homes, where patients with open wounds, invasive devices, and weakened immune systems are at greater risk of infection than the general public.

MRSA strains are prevalent bacterial pathogens that cause both health care- and community-associated infections. Increasing resistance to commonly prescribed antibiotics has made MRSA a serious threat to public health throughout the world. The USA300 strain of MRSA has been responsible for an epidemic of community-associated infections in the US, mostly involving skin and soft tissue but also more serious invasive syndromes such as pneumonia, severe sepsis and endocarditis. MRSA strains are particularly serious and potentially lethal pathogens that possess virulence mechanisms including toxins, adhesins, enzymes and immunomodulators. One of these is Panton-Valentine leukocidin (PVL), a toxin associated with abscess formation and severe necrotizing pneumonia.

Initially, MRSA strains afflicted hospitalized patients and those with chronic illnesses. The 1990s saw the emergence of community-associated MRSA (CA-MRSA) strains that primarily caused skin and soft tissue infections (SSTIs) in otherwise healthy individuals, often children. These strains quickly led to an epidemic of CA-MRSA infections including some with severe consequences, for example, community-acquired pneumonia with high mortality rates. The high prevalence of CA-MRSA among infecting MRSA strains in the US is mostly due to the Panton-Valentine leukocidin (PVL)-positive USA300 clone, while in Europe the predominant strain of CA-MRSA is a PVL-positive ST80 clone. A mathematical model predicted that CA-MRSA will become the dominant MRSA strain in hospitals because of the expanding community reservoir, CA-MRSA strains are more fit (higher replicative capacity) than hospital-associated types and that CA-MRSA infections will become increasingly severe (D'Agata et al., *Clin. Infect. Dis.* 48, 274-284, 2009).

Agents directed against the virulence mechanisms of MRSA strains would have several advantages compared to antibiotics. First, there would be no selective pressure exerted on other nonpathogenic, commensal bacteria. Second, the associated toxicities of antibiotics (e.g. allergic reactions, nephrotoxicity and *Clostridium difficile* infection) may be avoided. Third, limiting antibiotics may decrease the development of drug-resistant bacteria. Combining antivirulence therapies with traditional antibiotics has the potential to change the paradigm of how MRSA infections are managed. Since bacterial survival is not impacted by the function of its virulence mechanisms, it is possible that resistance to anti-virulence therapy would be slow to develop. One potential strategy is to inhibit the agr operon. In vitro experiments have shown that variants of autoinducing peptide (AIP) inhibit AgrC function. An in vivo study demonstrated that administering AIP-2 concurrently with an agr type 1 strain reduced abscess formation (Wright et al., *Proc. Natl. Acad. Sci. USA* 102, 1691-1696, 2005). However, agr inhibitors can promote biofilm formation, which could result in chronic *S. aureus* infections (Beenken et al., *PLoS ONE* 5, e10790, 2010). Hence, further investigation on this approach is needed.

Another strategy for devices is the use of nanomaterials, defined as materials with at least one dimension less than 100 nm, to prevent the formation of biofilms (Taylor & Webster, *Int. J. Nanomedicine* 6, 1463-1473, 2011). SilverPage lined urinary catheters and central venous catheters are used in clinical practice to lower the risk of health care-associated infections (Raad et al., *Antimicrob. Agents Chemother.* 56, 935-941, 2012). Decreasing the particle size of silver down to the nanometer range increases the surface area, which improves the antibacterial activity of the material (Taylor & Webster, *Int. J. Nanomedicine* 6, 1463-1473, 2011). Staphyloxanthin is a pigment of *S. aureus* that helps it resist reactive oxygen species such as those released by neutrophils. Early steps in staphyloxanthin production are similar to those in cholesterol production. A human squalene synthase inhibitor blocked staphyloxanthin biosynthesis in vitro, resulting in nonpigmented bacteria that were more susceptible to killing by human blood and clearance by the innate immune system in a mouse model (Liu et al., *Science* 319, 1391-1394, 2008). Statins were shown to enhance *S. aureus* clearance by phagocytes through production of antibacterial DNA-based extracellular traps by human and murine neutrophils, macrophages and monocytes (Chow et al., *Cell Host Microbe* 8, 445-454, 2010).

For CA-MRSA infections, one specific target is PVL toxin, and antibody against it is under investigation as a potential vaccine. However, in a study on antibody levels against PVL in children with PVL-positive MRSA infections, neutralizing antibody against PVL was not protective against primary or recurrent CA-MRSA skin infections (Hermos et al., *Clin. Infect. Dis.* 51, 1138-1146, 2010). Other investigators, using a murine model of dermonecrosis, evaluated an agonist of human C5a called EP67 for its ability to induce host immunity against CA-MRSA (Sheen et al., *Vaccine* 30, 9-13, 2011). EP67 was effective in limiting the infection through the promotion of cytokine synthesis and neutrophil influx. This promising finding may warrant further investigation in humans.

Peptidoglycan (PG) comprises approximately 50% of the cell wall of *S. aureus*. A PG-based vaccine against *S. aureus*, A170PG, was shown to be protective in a mouse model against several strains of MRSA including A174, A175, A176 and RIMD31092 (Capparelli et al., *PLoS ONE* 6, e28377, 2011). The protection correlated with increased survival and reduced colonization and lasted at least 40 weeks. One caveat with this study is that the mouse strain used does not closely mimic human infection because mice do not have pre-existing antibodies to *S. aureus*. In June 2011, Merck and Intercell announced the termination of phase II/III development of V170, a subunit vaccine containing the *S. aureus* antigen IsdB, which is a cell surface localized iron-regulated protein (Etz et al., *Proc. Natl. Acad. Sci. USA* 99, 6573-6578, 2002). Safety concerns were cited due to an increase in overall mortality and multi-organ dysfunction in the vaccine recipients compared to those who received placebo.

SUMMARY

The present disclosure provides a fully human antibody of an IgG class that binds to an AIP2 epitope with a binding affinity of at least $10^{-6}$M, which has a heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called A9 herein), SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein), SEQ ID NO. 9/SEQ ID NO. 10 (called F7 herein), SEQ ID NO. 11/SEQ ID NO. 12 (called G3 herein), SEQ ID NO. 13/SEQ ID NO. 14 (called G4 herein), SEQ ID NO. 15/SEQ ID NO. 16 (called H1 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof. Preferably, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, and combinations thereof.

The present disclosure further provides a method for treating or preventing the *S. aureus* infection comprising administering an anti-AIP2 polypeptide, wherein the fully human antibody has a heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has a light chain variable domain sequence that is at least 95% identical to the amino acid consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called A9 herein), SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein), SEQ ID NO. 9/SEQ ID NO. 10 (called F7 herein), SEQ ID NO. 11/SEQ ID NO. 12 (called G3 herein), SEQ ID NO. 13/SEQ ID NO. 14 (called G4 herein), SEQ ID NO. 15/SEQ ID NO. 16 (called H1 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called A9 herein), SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein), SEQ ID NO. 9/SEQ ID NO. 10 (called F7 herein), SEQ ID NO. 11/SEQ ID NO. 12 (called G3 herein), SEQ ID NO. 13/SEQ ID NO. 14 (called G4 herein), SEQ ID NO. 15/SEQ ID NO. 16 (called H1 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, and combinations thereof.

Preferably, the method for treating or preventing the *S. aureus* infection is caused by a MRSA *S. aureus* bacteria.

DETAILED DESCRIPTION

Figure 1:
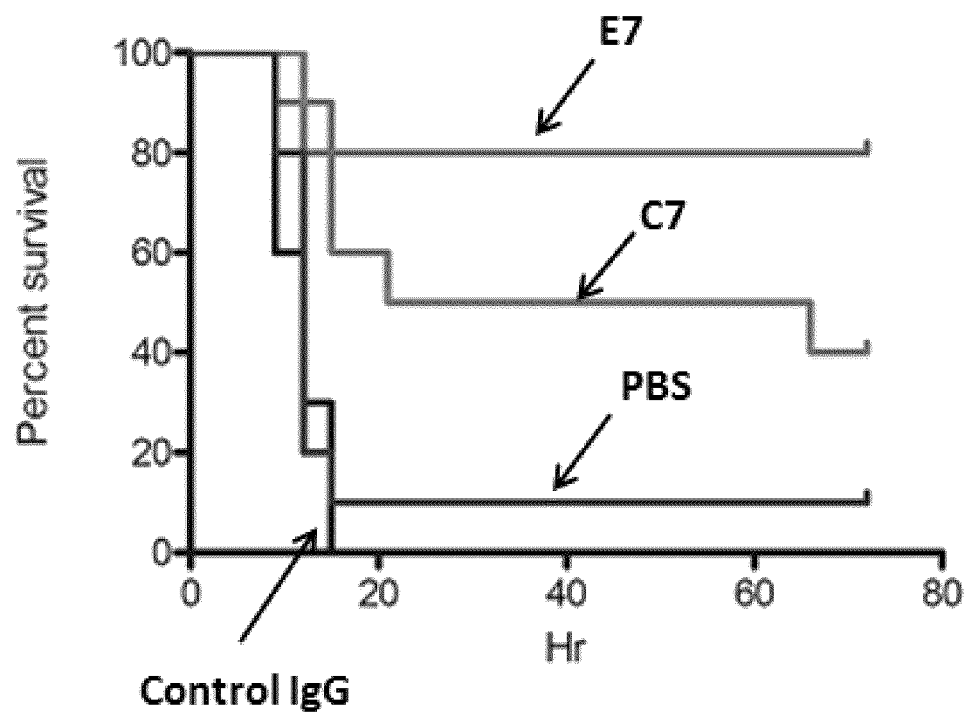
FIG. 1 shows that human anti-AIP mAbs C7 and E7 reduced mortality in mice infected intraperitoneally with USA100. *P≤0.0006 and 0.0008 versus control IgG and E7 or C7 respectively as determined by Log Rank test

The present disclosure provides a fully human antibody of an IgG class that binds to a AIP2 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called A9 herein), SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein), SEQ ID NO. 9/SEQ ID NO. 10 (called F7 herein), SEQ ID NO. 11/SEQ ID NO. 12 (called G3 herein), SEQ ID NO. 13/SEQ ID NO. 14 (called G4 herein), SEQ ID NO. 15/SEQ ID NO. 16 (called H1 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, and combinations thereof.

The present disclosure further provides a method for treating or preventing the S. aureus infection comprising administering an anti-AIP2 polypeptide, wherein the anti-AIP2 polypeptide is selected from the group consisting of a fully human antibody of an IgG class that binds to a AIP2 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has the light chain variable domain sequence that is at least 95% identical to the amino acid sequence consisting SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 15, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, and combinations thereof.

Preferably, method for treating or preventing the S. aureus infection is caused by a MRSA bacteria.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, US App. Pub. 20/0202512; 2004/0202995; 2004/0038291; 2004/0009507; 2003/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-AIP2 antibody. In another embodiment, all of the CDRs are derived from a human anti-AIP2 antibody. In another embodiment, the CDRs from more than one human anti-AIP2 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-AIP2 antibody, and the CDRs from the heavy chain from a third anti-AIP2 antibody. Other combinations are possible.

Further, the framework regions may be derived from one of the same anti-AIP2 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind AIP2).

A "neutralizing antibody" or an "inhibitory antibody" is an antibody that inhibits the proteolytic activation of AIP2 when an excess of the anti-AIP2 antibody reduces the amount of activation by at least about 20% using an assay such as those described herein in the Examples. In various embodiments, the antigen binding protein reduces the amount of amount of proteolytic activation of AIP2 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human AIP2) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*. 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

AIP2-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_n-CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Formulations and Modes of Administration

The present disclosure features method for treating or preventing the *S. aureus* infection comprising administering an anti-AIP2 polypeptide. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplary Uses

An AIP2 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-AIP2 antibodies agents of the invention can be used alone.

In certain embodiments, the binding polypeptides of fragments thereof can be labeled or unlabeled for diagnostic purposes. Typically, diagnostic assays entail detecting the formation of a complex resulting from the binding of a binding polypeptide to AIP2. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a AIP2 protein is combined with the subject binding polypeptides, binding occurs between the binding polypeptides and the AIP2 protein. In one embodiment, a sample containing cells expressing an AIP2 protein (e.g., endothelial cells) is combined with the subject antibodies, and binding occurs between the binding polypeptides and cells bearing a AIP2 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of an AIP2 protein in a biological sample can also be prepared. Such kits will include an AIP2 binding polypeptide which binds to an AIP2 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The following terms, unless otherwise indicated, shall be understood to have the following meanings:

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-EGFR antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human AIP2) if it binds to the antigen with a dissociation constant of 1 nanomolar or less.

An "antigen binding domain, "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to AIP2.

Oligomers that contain one or more antigen binding proteins may be employed as AIP2 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have AIP2 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a AIP2 binding fragment of an anti-AIP2 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-AIP2 antibody fragment or derivative fused to a leucine zipper peptide are expressed in suitable host cells, and the soluble oligomeric anti-AIP2 antibody fragments or derivatives that form are recovered from the culture supernatant.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to AIP2. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against AIP2 can be used, for example, in assays to detect the presence of AIP2 polypeptides, either in vitro or in vivo. The antigen binding proteins also may be employed in purifying AIP2 proteins by immunoaffinity chromatography. Blocking antigen binding proteins can be used in the methods disclosed herein. Such antigen binding proteins that function as AIP2 antagonists may be employed in treating any AIP2-induced condition, including but not limited to various cancers.

Antigen binding proteins may be employed in an in vitro procedure, or administered in vivo to inhibit AIP2-induced biological activity. Disorders caused or exacerbated (directly or indirectly) by the proteolytic activation of AIP2, examples of which are provided herein, thus may be treated. In one embodiment, the present invention provides a therapeutic method comprising in vivo administration of a AIP2 blocking antigen binding protein to a mammal in need thereof in an amount effective for reducing an AIP2-induced biological activity.

Antigen binding proteins include fully human monoclonal antibodies that inhibit a biological activity of AIP2.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or *bacilli*. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of AIP2 bound thereto. Polypeptides contemplated for use herein include substantially homogeneous recombinant mammalian anti-AIP2 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-AIP2 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for AIP2 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from AIP2. In one embodiment, the antigen binding protein has a $K_{off}$ of $1\times10^{-4}$ to $^{-1}$ or lower. In another embodiment, the $K_{off}$ is $5\times10^{-5}$ to $^{-1}$ or lower. In another embodiment, the $K_{off}$ is substantially the same as an antibody described herein. In another embodiment, the antigen binding protein binds to AIP2 with substantially the same $K_{off}$ as an antibody described herein.

In another aspect, the present disclosure provides an antigen binding protein that inhibits an activity of AIP2. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of AIP2 with substantially the same $IC_{50}$ as an antibody described herein.

In another aspect, the present disclosure provides an antigen binding protein that binds to human AIP2 expressed on the surface of a cell and, when so bound, inhibits AIP2 signaling activity in the cell without causing a significant reduction in the amount of AIP2 on the surface of the cell. Any method for determining or estimating the amount of AIP2 on the surface and/or in the interior of the cell can be used. In other embodiments, binding of the antigen binding protein to the AIP2-expressing cell causes less than about 75%, 50%, 40%, 30%, 20%, 15%, 10%, 5%, 1%, or 0.1% of the cell-surface AIP2 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of AIP2, or to an epitope of AIP2 and an epitope of another molecule, via two different antigen binding sites or regions. Moreover, bispecific antigen binding protein as disclosed herein can comprise an AIP2 binding site from one of the herein-described antibodies and a second AIP2 binding region from another of the herein-described antibodies, including those described herein by reference to other publications. Alternatively, a bispecific antigen binding protein may comprise an antigen binding site from one of the herein described antibodies and a second antigen binding site from another AIP2 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly (n-vinyl pyrrolidone), polyethylene glycols, propropylene glycol homopolymers, polypropylene oxide/ethylene oxide co-polymers, polyoxyethylated polyols and polyvinyl alcohols.

Example 1

Antibodies were immobilized on CM5 sensor chip using standard NHS/EDC coupling methodology. All measurements were conducted in HBS-EP buffer with a flow rate of 30 µL/min. AIP2 was diluted so as to obtain a series of concentrations. A 1:1 (Langmuir) binding model was

TABLE 1

| mAb | $K_{on}$ | $K_{off}$ | $K_d$ |
|---|---|---|---|
| C7 | 3.08E+5 | 0.016 | 52 nM |
| D3 | 5.22E+5 | 0.0254 | 49 nM |
| E7 | 1.15E+6 | 0.0736 | 64 nM | used to fit the data.

Example 2

This example shows quorum quenching using *S. aureus* agr-driven YFP reporter strains. *S. aureus* strains (transformed with the reporter plasmid pDB59) representing agr group I (USA300/LAC), agr group II (USA100), and agr group IV (MnTG). All *S. aureus* reporter strains were grown overnight in tryptic soy broth supplemented with chloramphenicol at 10 µg/mL at 37° C. with shaking. For antibody inhibition testing, cultures were diluted 100-fold into fresh media, incubated for 1 hour at 37° C., and 180 µL was dispensed into wells of a 96-well microtiter plate. The anti-AIP 2 mAbs were diluted to a working concentration of 3 mg/mL in PBS, and 3-fold serial dilutions were generated in PBS to a final concentration of $4.6 \times 10^{-4}$ mg/mL. 20 µL of each antibody dilution was added to the reporter cultures in the microtiter plates in triplicate, resulting in an additional 10-fold dilution. As controls, PBS was used as a mock treated sample (no antibody). Plates were incubated for 22 h at 37° C. with shaking at 250 rpm. Absorbance and fluorescence was measured in a plate reader using an excitation wavelength of 485 nm and an emission wavelength of 530 nm.

TABLE 2

| mAb | Inhibition of AIP1 QS (IC$_{50}$; nM) | Inhibition of AIP2 QS (IC$_{50}$; nM) | Inhibition of AIP4 QS (IC$_{50}$; nM) |
|---|---|---|---|
| C7 | 109.9 (USA300 - LAC) | 33.7 (USA100 - AH2619) 31.2 (USA100 - AH2625) | 86 (MnTG) |
| E7 | 91.1 (USA300 - LAC) | 34.2 (USA100 - AH2619) 31.02 (USA100 - AH2625) | 53.5 (MnTG) |

Example 3

This example shows mitigation of a MRSA lethal peritonitis infection model. The *S. aureus* strain USA100 was harvested at mid-exponential growth phase washed in sterile Dulbecco's phosphate buffered saline (DPBS) and resuspended in sterile DPBS. To test the efficacy of the anti-AIP2 antibodies against a lethal challenge with *S. aureus* USA100, mice were pretreated for one-hour with 1 mg of antibody via intraperitoneal (i.p.) inoculation. After pre-treatment all mice were infected i.p. with 100 µL containing $5.5 \times 10^7$ colony forming units (CFUs) for infections with USA100. Mice were monitored every 3 h for the first 48 h and then twice per day for 72 hours. If the animals were immobile or unable to eat or drink, they were euthanized. Pre-treatment with both C7 and E7 resulted in decreases in lethality (FIG. 1). Remarkably, mice pre-treated with E7 had an 80% survival rate compared to 0 and 10% survival in control IgG and PBS control groups.

Example 4

Figure 2:
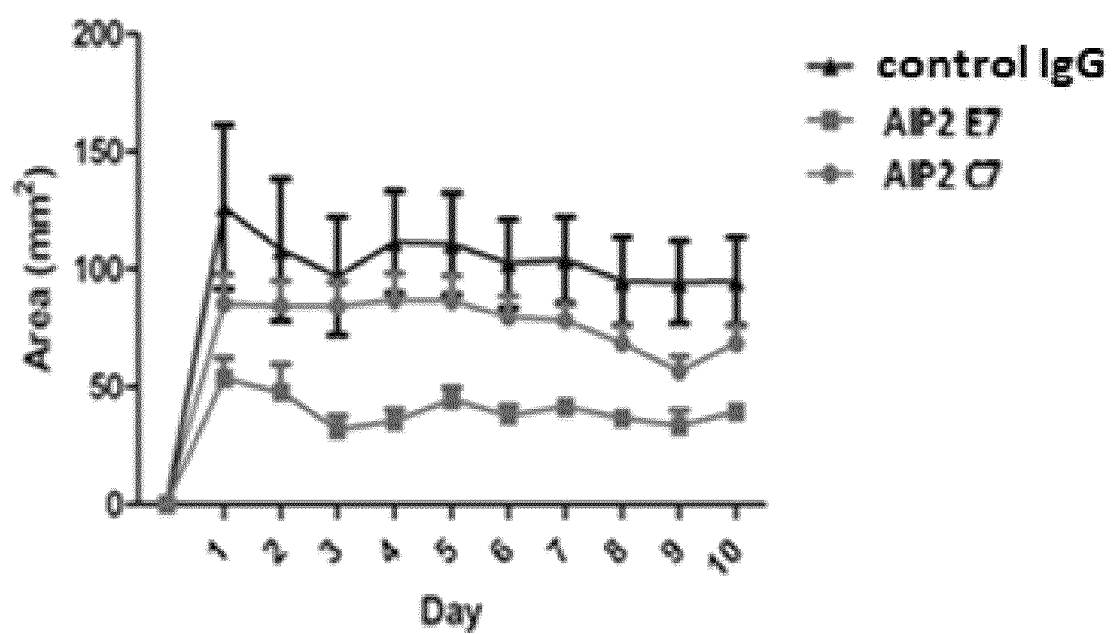
FIG. 2 shows that human anti-AIP mAbs C7 and E7 reduced abscess size in mice infected with USA100. *P≤0.01-0.04, E7 versus control on all days tested as determined by paired T-test.

This example shows mitigation of a MRSA skin and soft tissue infection (SSTI) in a mouse model. For the SSTI model, BALB/c mice (8 mice per treatment group) were shaved and infected subcutaneously with $2 \times 10^6$ USA100 mixed with 1 mg of C7, E7, control mAb, or PBS. Infected area was measured daily for 10 days. Treatment with E7 caused significant reduction in abscess size at all days tested (FIG. 2).

Example 5

Figure 3:
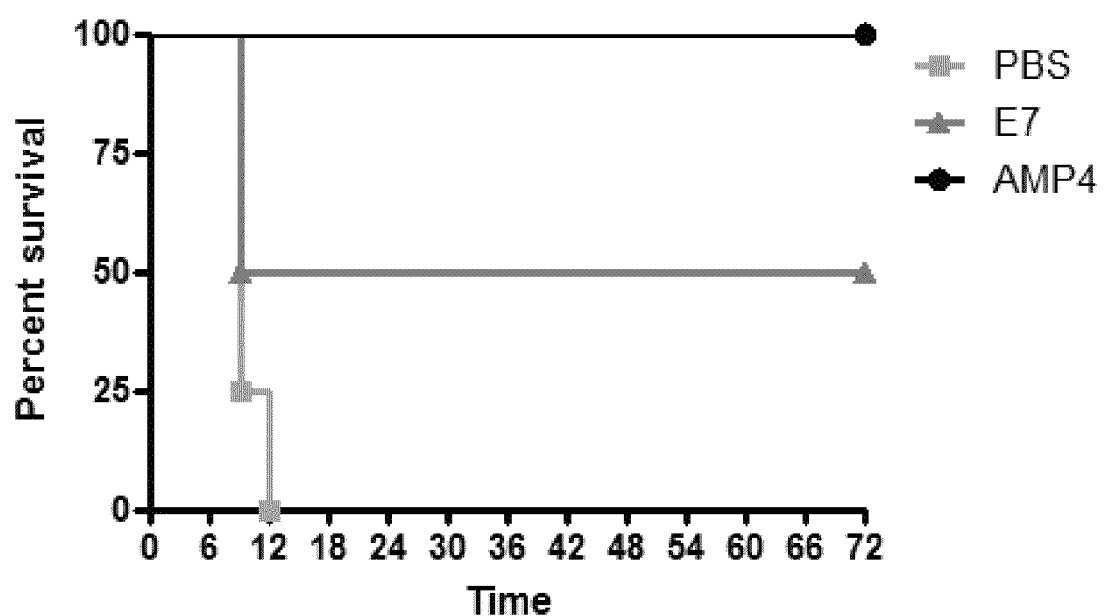
FIG. 3 shows that human anti-AIP mAb E7 reduced mortality in mice infected intraperitoneally with MSSA RN4850.

This example shows mitigation of a MSSA lethal peritonitis infection model. The *S. aureus* strain RN4850, which produced AIP4, was harvested at mid-exponential growth phase washed in sterile Dulbecco's phosphate buffered saline (DPBS) and resuspended in sterile DPBS. To test the efficacy of the anti-AIP2 antibodies against a lethal challenge with an AIP4-producing *S. aureus* RN4850, mice were pretreated for one-hour with 1 mg of antibody via intraperitoneal (i.p.) inoculation. After pre-treatment all mice were infected i.p. with 100 µL containing $2 \times 10^8$ colony forming units (CFUs) for infections with RN4850. Mice were monitored every 3 h for the first 48 h and then twice per day for 72 hours. If the animals were immobile or unable to eat or drink, they were euthanized. Pre-treatment with E7 resulted in decreases in lethality (FIG. 3). Remarkably, mice pre-treated with E7 had a 50% survival rate compared to 10% and 0% survival in control IgG and PBS control groups, respectively. These data demonstrate that the anti-AIP2 mAb E7 confers cross-protection against an AIP4-producing *S. aureus* strain.

We claim:

1. A fully human antibody of an IgG class that binds to *S. aureus* auto inducing peptide-2 (AIP2) with a binding affinity of at least $10^{-6}$ M, wherein the antibody has a heavy chain/light chain variable domain sequence that is at least 95% identical to the amino acid sequences selected from the group consisting of SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein).

2. A Fab fully human antibody fragment that binds to *S. aureus* auto inducing peptide-2 (AIP2) with a binding affinity of at least $10^{-6}$ M, wherein the antibody has a heavy chain/light chain variable domain sequence that is at least 95% identical to the amino acid sequences selected from the croup consisting of SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein).

3. A single chain human antibody that binds to *S. aureus* auto inducing peptide-2 (AIP2) with a binding affinity of at least $10^{-6}$ M, having a variable domain region from a heavy chain and a variable domain region from a light chain and a peptide linker connection the heavy chain and light chain variable domain regions, wherein the antibody has a heavy chain/light chain variable domain sequence that is at least 95% identical to the amino acid sequences selected from the croup consisting of SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein).

4. A method for treating a *S. aureus* infection, comprising administering an effective amount of an anti-AIP2 polypeptide, wherein the anti-AIP2 polypeptide is selected from the group consisting of a fully human antibody of an IgG class that binds to *S. aureus* auto inducing peptide-2 (AIP2) with a binding affinity of at least $10^{-6}$ M, wherein the antibody has a heavy chain/light chain variable domain sequence that is at least 95% identical to the amino acid sequences selected from the croup consisting of SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein); a Fab fully human antibody fragment, wherein the antibody has a heavy chain/light chain variable domain sequence that is at least 95% identical to the amino acid sequences selected from the group consisting of SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein); and a single chain human antibody, having a variable domain region from a heavy chain and a variable domain region from a light chain and a peptide linker connection the heavy chain and light chain variable domain regions, wherein the antibody has a heavy chain/light chain variable domain sequence that is at least 95% identical to the amino acid sequences selected from the group consisting of SEQ ID NO. 3/SEQ ID NO. 4 (called C7 herein), SEQ ID NO. 5/SEQ ID NO. 6 (called D3 herein), SEQ ID NO. 7/SEQ ID NO. 8 (called E7 herein).

5. The method for treating a *S. aureus* infection of claim 4, wherein the *S. aureus* infection is caused by MRSA.

\* \* \* \* \*

SEQUENCE LISTING

<160> NUMBER OF SEQ ID NOS: 16

<210> SEQ ID NO 1
<211> LENGTH: 113
<212> TYPE: PRT
<213> ORGANISM: Homo sapiens

<400> SEQUENCE: 1

Glu Val Gln Leu Val Glu Ser Gly Gly Gly Leu Ile Gln Ser Gly Gly
1               5                   10                  15

Ser Leu Arg Leu Ser Cys Ala Ala Ser Gly Phe Thr Val Thr Thr Asn
            20                  25                  30

Tyr Met Ser Trp Val Arg Gln Ala Pro Gly Lys Gly Leu Glu Trp Val
        35                  40                  45

Ser Ile Thr Gln Ser Gly Gly Ala Thr Tyr Tyr Ala Asp Ser Val Lys
    50                  55                  60

Gly Arg Phe Thr Ile Ser Arg Asp Ile Ser Lys Asn Thr Leu His Leu
65                  70                  75                  80

Gln Met Asn Ser Leu Arg Val Glu Asp Thr Ala Met Tyr Tyr Cys Ala
                85                  90                  95

Arg Gly Asp Phe Asp Tyr Trp Gly Gln Gly Thr Leu Val Thr Val Ser
            100                 105                 110

Ser

<210> SEQ ID NO 2
<211> LENGTH: 110
<212> TYPE: PRT
<213> ORGANISM: Homo sapiens

<400> SEQUENCE: 2

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Met Tyr Arg Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Phe Cys Ala Ala Trp Asp Asp Ser Leu
                85                  90                  95

Ser Gly Val Val Phe Gly Gly Gly Thr Lys Leu Thr Val Leu
            100                 105                 110

<210> SEQ ID NO 3
<211> LENGTH: 115
<212> TYPE: PRT
<213> ORGANISM: Homo sapiens

<400> SEQUENCE: 3

Glu Val Gln Leu Val Gln Ser Gly Ala Glu Met Lys Lys Pro Gly Ala
1               5                   10                  15

Ser Met Lys Val Ser Cys Lys Thr Ser Gly Tyr Thr Phe Ala Arg Lys
            20                  25                  30

Tyr Met His Trp Leu Arg Gln Ala Pro Gly Gln Gly Leu Glu Trp Met
        35                  40                  45

-continued

```
Gly Ile Ile Asn Pro Thr Gly Gly Thr Lys Ser Tyr Ala Pro Lys Phe
        50                  55                  60

Gln Gly Arg Val Thr Met Thr Ser Asp Met Ser Thr Asn Thr Val Tyr
 65                  70                  75                  80

Met Glu Leu Asn Ser Leu Arg Ser Glu Asp Thr Ala Val Tyr Tyr Cys
                 85                  90                  95

Val Ser Asp Asp Glu Glu Pro Val Trp Gly Gln Gly Thr Met Val Thr
                100                 105                 110

Val Ser Ser
        115

<210> SEQ ID NO 4
<211> LENGTH: 110
<212> TYPE: PRT
<213> ORGANISM: Homo sapiens

<400> SEQUENCE: 4

Gln Ser Ala Leu Thr Gln Pro Pro Ser Val Ser Lys Gly Leu Arg Gln
 1               5                  10                  15

Thr Ala Thr Leu Thr Cys Thr Gly Asn Ser Asn Asn Val Gly Ser Gln
                 20                  25                  30

Gly Ala Ala Trp Leu Gln Gln His Gln Gly His Pro Pro Lys Val Leu
             35                  40                  45

Ser Tyr Arg Asn Asn Arg Pro Ser Gly Ile Ser Glu Arg Phe Ser
         50                  55                  60

Ala Ser Arg Ser Gly Asn Thr Ala Ser Leu Thr Ile Thr Gly Leu Gln
 65                  70                  75                  80

Pro Glu Asp Glu Gly Asp Tyr Tyr Cys Ser Ala Trp Asp Ser Ser Leu
                 85                  90                  95

Ser Ala Pro Val Phe Gly Gly Gly Thr Lys Leu Thr Val Leu
                100                 105                 110

<210> SEQ ID NO 5
<211> LENGTH: 124
<212> TYPE: PRT
<213> ORGANISM: Homo sapiens

<400> SEQUENCE: 5

Glu Val Gln Leu Val Gln Ser Gly Ala Glu Val Lys Lys Pro Gly Ser
 1               5                  10                  15

Ser Val Lys Val Ser Cys Lys Ala Tyr Gly Gly Thr Phe Gly Ser Tyr
                 20                  25                  30

Gly Val Ser Trp Val Arg Arg Ala Pro Gly Gln Gly Leu Glu Trp Met
             35                  40                  45

Gly Arg Leu Ile Pro Ile Phe Gly Thr Arg Asp Tyr Ala Gln Lys Phe
         50                  55                  60

Gln Gly Arg Val Thr Leu Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Asp Tyr Tyr Gly Ser Gly Ser Tyr Tyr Gly Met Asp
                100                 105                 110

Val Trp Gly Gln Gly Thr Leu Val Thr Val Ser Ser
            115                 120

<210> SEQ ID NO 6
<211> LENGTH: 111
```

<212> TYPE: PRT
<213> ORGANISM: Homo sapiens

<400> SEQUENCE: 6

```
Ser Tyr Glu Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Val
            35                  40                  45

Met Ile Tyr Glu Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr His Val Val Phe Gly Gly Gly Thr Lys Val Thr Val Leu
                100                 105                 110
```

<210> SEQ ID NO 7
<211> LENGTH: 115
<212> TYPE: PRT
<213> ORGANISM: Homo sapiens

<400> SEQUENCE: 7

```
Glu Val Gln Leu Val Gln Ser Gly Ala Glu Val Lys Lys Pro Gly Ala
1               5                   10                  15

Ser Val Arg Val Ser Cys Lys Thr Ser Gly Tyr Ser Phe Thr Ser Tyr
                20                  25                  30

Asp Ile Asn Trp Val Arg Gln Thr Thr Gly Gln Gly Leu Glu Trp Met
            35                  40                  45

Gly Trp Val Asn Pro Thr Ser Gly Ser Thr Gly Tyr Ala Gln Lys Phe
        50                  55                  60

Gln Gly Arg Val Thr Met Thr Ala Asn Thr Ala Ile Asn Thr Ala Tyr
65                  70                  75                  80

Met Glu Leu Arg Asp Leu Arg Ser Glu Asp Thr Ala Val Tyr Phe Cys
                85                  90                  95

Val Arg Asp Val Pro Phe Asp Pro Trp Gly Gln Gly Thr Leu Val Thr
                100                 105                 110

Val Ser Ser
        115
```

<210> SEQ ID NO 8
<211> LENGTH: 111
<212> TYPE: PRT
<213> ORGANISM: Homo sapiens

<400> SEQUENCE: 8

```
Leu Gln Ser Val Leu Thr Gln Pro Ala Ser Val Ser Gly Ser Pro Gly
1               5                   10                  15

Gln Ser Ile Thr Ile Ser Cys Thr Gly Thr Ser Ser Asp Val Gly Lys
                20                  25                  30

Tyr Thr Phe Val Ser Trp Tyr Gln Gln His Pro Gly Lys Ala Pro Lys
            35                  40                  45

Val Met Val Tyr Glu Val Asn Lys Arg Pro Gly Val Ser Pro Arg
        50                  55                  60

Phe Ser Gly Ser Lys Ser Gly Asn Thr Ala Tyr Leu Thr Ile Ser Gly
```

```
                65                  70                  75                  80
Leu Gln Ala Glu Asp Glu Ala Asp Tyr Tyr Cys Ser Ser Tyr Thr Ser
                85                  90                  95

Ser Ser Thr Val Val Phe Gly Gly Gly Thr Lys Leu Thr Val Leu
            100                 105                 110

<210> SEQ ID NO 9
<211> LENGTH: 115
<212> TYPE: PRT
<213> ORGANISM: Homo sapiens

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Trp Ile Asn Pro Tyr Asn Gly Asn Ala Asn Tyr Ala Gln Lys Leu
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Gly Gly Ala Val Trp Gly Gln Gly Thr Thr Val Thr
            100                 105                 110

Val Ser Ser
        115

<210> SEQ ID NO 10
<211> LENGTH: 110
<212> TYPE: PRT
<213> ORGANISM: Homo sapiens

<400> SEQUENCE: 10

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Ser Trp Tyr Gln Gln His Pro Gly Lys Ala Pro Lys Val
        35                  40                  45

Met Ile Tyr Glu Val Ser Glu Arg Pro Ser Gly Val Ser Asn Arg Phe
    50                  55                  60

Ser Gly Ser Lys Ser Gly Asn Ala Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110

<210> SEQ ID NO 11
<211> LENGTH: 113
<212> TYPE: PRT
<213> ORGANISM: Homo sapiens

<400> SEQUENCE: 11

Glu Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Gln
            20                  25                  30

Tyr Met His Trp Val Arg Gln Ala Pro Gly Gln Gly Leu Glu Trp Met
        35                  40                  45

Gly Val Ile Asn Pro Asn Asp Gly Thr Thr Ser Tyr Ala Gln Lys Phe
 50                  55                  60

Gln Gly Arg Val Thr Met Thr Ser Asp Thr Phe Thr Ser Thr Val Tyr
 65                  70                  75                  80

Met Glu Leu Ser Asn Leu Arg Ser Asp Asp Thr Ala Val Phe Tyr Cys
            85                  90                  95

Ala Arg Asp Gly Asp Tyr Trp Gly Gln Gly Thr Leu Val Thr Val Ser
            100                 105                 110

Ser

<210> SEQ ID NO 12
<211> LENGTH: 112
<212> TYPE: PRT
<213> ORGANISM: Homo sapiens

<400> SEQUENCE: 12

Asp Ile Val Met Thr Gln Thr Pro Leu Ser Ser Pro Val Thr Leu Gly
1               5                   10                  15

Gln Pro Ala Ser Ile Ser Cys Arg Ser Ser His Ser Leu Val Asn Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Val
            85                  90                  95

Ser His Phe Pro Tyr Ala Phe Gly Gln Gly Thr Lys Leu Glu Ile Lys
            100                 105                 110

<210> SEQ ID NO 13
<211> LENGTH: 121
<212> TYPE: PRT
<213> ORGANISM: Homo sapiens

<400> SEQUENCE: 13

Gln Val Gln Leu Val Glu Ser Gly Ala Glu Val Arg Lys Pro Gly Ser
1               5                   10                  15

Ser Val Lys Val Ser Cys Lys Ala Ser Gly Asp Thr Phe Arg Ser Tyr
            20                  25                  30

Gly Val Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
            85                  90                  95

Ala Arg Glu Val Gly Ala Arg Gly Glu Tyr Phe Gln His Trp Gly
            100                 105                 110

```
Gln Gly Thr Leu Val Thr Val Ser Ser
            115                 120
```

<210> SEQ ID NO 14
<211> LENGTH: 110
<212> TYPE: PRT
<213> ORGANISM: Homo sapiens

<400> SEQUENCE: 14

```
Leu Pro Val Leu Thr Gln Pro Arg Ser Val Ser Gly Ser Pro Gly Gln
1               5                   10                  15

Ser Val Thr Ile Ser Cys Thr Gly Thr Thr Ser Asp Val Gly Asn Tyr
            20                  25                  30

His Tyr Val Ser Trp Tyr Arg Gln His Pro Gly Lys Ala Pro Lys Leu
        35                  40                  45

Met Met Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Thr Ser Thr
                85                  90                  95

Asn Ser Val Ile Phe Gly Gly Gly Thr Lys Leu Thr Val Leu
            100                 105                 110
```

<210> SEQ ID NO 15
<211> LENGTH: 115
<212> TYPE: PRT
<213> ORGANISM: Homo sapiens

<400> SEQUENCE: 15

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Thr Tyr
            20                  25                  30

Gly Ile His Trp Val Arg Gln Ala Pro Gly Gln Gly Leu Glu Trp Met
        35                  40                  45

Gly Trp Leu Asn Thr His Thr Glu His Pro Thr Tyr Ala Gln Gly Phe
    50                  55                  60

Thr Gly Arg Phe Val Leu Ser Leu Asp Thr Ser Val Ser Thr Ala Tyr
65                  70                  75                  80

Leu Gln Ile Thr Ser Leu Lys Ala Glu Asp Thr Ala Val Tyr Tyr Cys
                85                  90                  95

Val Arg Asp Asp Ser Phe Asp Pro Trp Gly Pro Gly Thr Leu Val Thr
            100                 105                 110

Val Ser Ser
        115
```

<210> SEQ ID NO 16
<211> LENGTH: 109
<212> TYPE: PRT
<213> ORGANISM: Homo sapiens

<400> SEQUENCE: 16

```
Tyr Glu Leu Thr Gln Pro Ala Ser Val Ser Gly Ser Pro Gly Gln Ser
1               5                   10                  15

Val Thr Ile Ser Cys Thr Gly Thr Ser Ser Asp Ile Gly Ala Tyr Asn
            20                  25                  30

Phe Val Gly Trp His Gln Gln His Pro Gly Lys Ala Pro Lys Leu Met
```

```
                    35                      40                          45

Ile Phe Asp Val Ser Asn Arg Pro Ser Gly Val Ser Ser Arg Phe Ser
        50                      55                  60

Gly Ser Lys Ser Gly Asn Thr Ala Ser Leu Thr Ile Ser Gly Leu Gln
65                      70                  75                      80

Ala Glu Asp Glu Ala Asp Tyr Tyr Cys Ser Ser Tyr Thr Thr Ser Ser
                85                  90                  95

Thr Val Ala Phe Gly Gly Gly Thr Lys Val Thr Val Leu
            100                 105
```